United States Patent
Benson et al.

(10) Patent No.: US 7,435,166 B2
(45) Date of Patent: Oct. 14, 2008

(54) METHODS AND DEVICES FOR DEPOPULATING AVIAN SPECIES

(75) Inventors: Eric R. Benson, Baltimore, MD (US); Robert L. Alphin, Chesapeake City, MD (US); George W. Malone, Princess Anne, MD (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 11/654,190

(22) Filed: Jan. 17, 2007

(65) Prior Publication Data

US 2007/0184081 A1    Aug. 9, 2007

Related U.S. Application Data

(60) Provisional application No. 60/759,666, filed on Jan. 18, 2006.

(51) Int. Cl.
*A22C 18/00*    (2006.01)
(52) U.S. Cl. ...................................................... 452/173
(58) Field of Classification Search .................. 452/173
See application file for complete search history.

(56) References Cited

U.S. PATENT DOCUMENTS

| | | | |
|---|---|---|---|
| 4,741,121 A | 5/1988 | Pratscher et al. |
| 5,857,627 A | 1/1999 | Horwell et al. |
| 5,902,597 A | 5/1999 | Iwakawa et al. |

FOREIGN PATENT DOCUMENTS

WO    WO2007/021178    2/2007

OTHER PUBLICATIONS

A1 Kifco Aviguard Foamer Poultry disease control-safe and simple Product Brochure, Jul. 2006.*
A2 Kifco Aviguard Foamer Poultry disease control-safe and simple Additional Product Brochure, Jul. 2006.*
A3 Smith Irrigation Equipment Traveling Sprinkler Systems. 2004.*
Benson. E.R., G.W. Malone, R.L. Alphin, M.D. Dawson, C.R. Pope, and G. L. Van Wicklen. 2007. Foam-based mass emergency depopulation of floor-reared meat-type poultry operations. Poult. Sci. 86:219-224.
Dawson, M.D., P.L. Reyes, E.R. Benson, R.L. Alphin, G.W. Malone, G.L. Van Wicklen, and I. Estevez. 2006. Evaluation of foam-based depopulation methodology for floor-reared meat-type poultry operations. Appl. Engi. in Agric. 22(5):787-794.

(Continued)

*Primary Examiner*—Thomas Price
(74) *Attorney, Agent, or Firm*—McCarter & English, LLP

(57) ABSTRACT

A method of depopulating livestock is provided. The method comprises restricting the livestock in a defined space, and depositing foam into the defined space, forming a foam blanket covering the livestock. The livestock can be avians, such as chickens, ducks, and turkeys. A device for making medium expansion foam comprising a high expansion foam generator having a fan, and a shroud shielding the fan from ambient air intake. The shroud limits the amount of ambient air incorporated into the foam during operation. The device can include an alternative gas input positioned to direct an alternative gas to the fan. The alternative gas is selected from the group consisting of carbon dioxide, nitrogen, argon, and mixtures thereof.

23 Claims, 5 Drawing Sheets

OTHER PUBLICATIONS

M. D. Dawson, M. E. Lombardi, E. R. Benson, R. L. Alphin, and G.W. Malone. 2007. Validation of the Use of Accelerometers in the Determination of Post-Mortem Muscular Cessation in Euthanized and Depopulated Poultry. Journal of Applied Poultry Research. Resubmitted Jul. 13, 2007.

M.D. Dawson, P.L. Reyes, E.R. Benson, R.L. Alphin, G.W. Malone, G.L. Van Wicklen and I. Estevez. 2005. Evaluating the Use of Fire Fighting Foam in Mass Poultry Euthanasia. ASAE Paper No. 054001. St. Joseph, MI: ASAE.

Gerritzen, M.A., Lambooij, E., Reimert, H., A. Stegeman, A., Spruijt, B. (2004). On Farm Euthanasia of Broiler Chicken: effects of Different gas Mixtures On Behavior and Brain Activity, Poultry Science 83: 1294-1301.

Gerritzen, M.A., Lambooij, E., Reimert, H.G.M., Spruijt, B.M., Stegeman, A. (2006) . Susceptibility of Ducks and Turkeys to Severe Hypercapnic Hypoxia. Poultry Science 85:1055-1061.

Kingston, S.K., C.A. Dussalt, R.S. Zaaidlicz, N.H. Faltas, M.E. Geib, S. Taylor, T. Holt, and B.A. Porter-Spalding. 2005. Evaluation of two methods for mass euthanasia of poultry in disease outbreaks. J. Am. Vet. Med. Assoc. 227 (5): 730-738.

\* cited by examiner

METHODS AND DEVICES FOR DEPOPULATING AVIAN SPECIES

CROSS REFERENCE TO RELATED APPLICATIONS

The present application claims the benefit of U.S. Provisional Application Ser. No. 60/759,666 filed Jan. 18, 2006, the disclosure of which is expressly incorporated herein by reference in its entirety.

FIELD OF THE INVENTION

The invention relates to methods and devices for mass depopulation of livestock. Specifically, the invention relates to the use of foam for mass depopulation of avians.

BACKGROUND OF THE INVENTION

Livestock disease outbreaks are a serious threat to human and animal safety. For example, since 1999, there have been twenty-six avian influenza episodes involving twenty-five countries. These episodes required destroying of over 132 million birds and vaccinating an additional 1.9 billion birds. Avian influenza (AI) poses a significant threat to the United States poultry industry. One of the worst AI cases in recent U.S. history occurred in Pennsylvania in 1983, in which an outbreak of high pathogenic avian influenza (HPAI), H5N2, resulted in the destruction of 17 million birds at a cost of $61 million. In 2002, a low pathogenic avian influenza (LPAI), H7N2, outbreak in Virginia resulted in the destruction of 4.7 million birds at a cost of $160 million. The detection of two separate H7N2 LPAI strains in the Delmarva region in 2004 resulted in the destruction of 328,000 birds on two farms in Maryland and 85,000 birds on two farms in Delaware. A HPAI H5N2 outbreak in Gonzales County, Texas required depopulation of 6,608 broilers as a control measure.

Control of avian influenza consists of detection, confinement and depopulation or vaccination of the affected region. Quarantine of the area is an immediate step in control of an infectious poultry disease and can significantly reduce the spread of the disease. Birds that are infected or suspected of infection are depopulated using the most expedient method possible. Vaccination has been used in control of several outbreaks, however, the usefulness of conventional vaccination as an eradication tool remains unclear. Evidence indicates that the virus can continue to replicate in clinically healthy vaccinated birds, which reduces the effectiveness of vaccination programs. In addition, avian influenza is highly mutagenic, which can result in divergence between the vaccination strain and infection strain. For this reason, depopulation remains the primary control measures for avian influenza. Depopulation of poultry includes the euthanasia of the birds, removal of the carcasses and litter and decontamination or disinfecting of the facility and/or equipment.

Depopulation is also required to control outbreaks of other diseases. Exotic Newcastle Disease is an example of another avian disease where depopulation of infected birds and birds suspected of infection is a primary control measure.

Emergency depopulation of livestock is necessary under other conditions, such as natural disasters. Natural disasters, such as hurricanes, tornadoes, earthquakes, snow, wind, and floods, can damage livestock housing, leading to a need to quickly and efficiently depopulate livestock houses that are unsafe for human entry. For example, when poultry housing has been damaged such that food and water cannot be provided to the animals, the animals must be depopulated in a humane and safe manner.

Although a quick response is desired in the event of a disease outbreak, depopulation of birds must be performed in a humane manner. Depopulation and euthanasia describe similar applications. The American Veterinary Medical Association (AVMA) describes euthanasia as "rapid loss of consciousness followed by cardiac or respiratory arrest and the ultimate loss of brain function." (2000 Report of the AVMA panel on euthanasia. JAVMA 218(5): 669-698.) The AVMA requires that the animal(s) to be euthanized experience minimal distress before being rendered unconscious. There are a number of currently accepted methods for euthanizing poultry include inhalation agents, non-penetrating captive bolt, cervical dislocation, percussive blow, decapitation, maceration, and electrocution. The methods cause death by (1) direct or indirect hypoxia, (2) direct depression of neurons and/or (3) physical disruption of brain activity. Extensive guidelines exist for euthanasia of poultry for processing prior to marketing. However, during emergencies such as a disease outbreak, there are fewer options. The 2000 Report of the AVMA Panel on Euthanasia, devotes only one paragraph on mass euthanasia and states "[u]nder unusual conditions, such as disease eradication and natural disasters, euthanasia options may be limited. In these situations, the most appropriate technique that minimizes human and animal health concerns must be used."

Gassing is one of the accepted methods for euthanizing poultry. The gases most often employed include mixtures containing argon (Ar), nitrogen (N), carbon monoxide (CO), and/or carbon dioxide (CO2). Argon and nitrogen displace oxygen (O2) in the air, while CO2 directly affects the central nervous system.

Carbon dioxide is a well-known anesthetic gas that can induce rapid loss of consciousness, but at high concentrations (>65%) it is known to be an irritant to humans. Poultry are unable to detect the presence of CO2 before succumbing to the effects of the presence of high concentrations of the gas. The lack of reaction by the birds to the introduction of a gas falls within the suggested AVMA guidelines for the use of inhalants for euthanizing animals.

The AVMA has suggested that euthanasia is more humane if the animals are exposed to high concentrations of the inhalant so that unconsciousness is rapidly induced. In addition, the suggested exposure for optimal euthanasia is a five-minute period of exposure to CO2 in concentrations of 60 to 70 percent. Carbon dioxide stunning, however, is impractical as birds can regain consciousness in less than 30 seconds in some experiments.

Carbon dioxide-argon mixtures cause rapid loss of brain function in poultry. It has been suggested that moderate CO2 concentrations are more practical, particularly in on-farm applications. Emergency euthanasia, such as in the case of an AI outbreak, would need to be conducted on-site at the poultry farm to comply with quarantine regulations. Under field conditions, it is difficult to maintain a tightly governed range of gas concentrations.

Alternate gassing mixtures involving Ar or N rely on dilution of the oxygen in the surrounding atmosphere. Livestock houses are not airtight environments, and control of the environment is again a difficulty in those situations when emergency depopulation is necessary.

Several current industry procedures for large-scale emergency euthanasia consist of exposing poultry to CO2 gas while they are in the poultry house. Carbon dioxide gas causes rapid onset of anesthesia with subsequent death due to respiratory arrest. Portable panels with tarp covers were employed in the 2002 AI outbreak in Virginia. The panel enclosure was constructed inside the house and took 7 workers approximately 2 hours to construct per house. Groups of birds were driven and/or placed into theses units and euthanized with carbon dioxide. The panel enclosure method could be used for batches of up to 5,500 turkeys at a time and required between 6 to 10 minutes for audible signs of activity to cease.

A second procedure used for broilers in Virginia employed a metal container placed over a live-haul cage. The birds were caught by human catching crews and placed in a standard live-haul cage. After the cage was filled with birds, the cage was transported outside the building and a metal container was placed over the cage. Carbon dioxide gas was injected into the container. This method was also performed in a batch mode, with 375 chickens per batch, and required 1:00 to 1:40 (minutes:seconds) until audible signs of activity ceased.

A third procedure called the polyethylene tent method which has been used for broilers in Virginia and more recently on Delmarva. In the polyethylene tent procedure, the birds are condensed into one region of the house. Carbon dioxide cylinders are placed inside the euthanasia region and overlapping layers of polyethylene or other plastic sheeting are used the to cover birds. The polyethylene sheet is buried in the litter at the outside edge and overlapped in the region above the birds, forming a tent over the birds. After sealing the tent area, $CO_2$ is released into the tent area.

All procedures are very labor intensive and create significant biosecurity risks. For example, the live-haul cage procedure requires the catching crew to be placed in intimate contact with birds infected with a potentially zoonotic virus. With this procedure, infected birds are transported outside the house prior to euthanasia, increasing potential spread. Euthanizing a typical farm with 75,000 to 100,000 market age broilers with the polyethylene tent method in one day would require a labor and support staff estimated in excess of 40 people. Furthermore, the process requires a tractor and additional personnel to remove the polyethylene from the houses. When this material is removed from the house, it may be heavily contaminated with litter, carcasses and debris, creating another biosecurity risk. Disposal of the contaminated polyethylene sheet via sanitary landfill or on-site burning creates yet another challenge for the procedure. While these procedures were effectively used to destroy flocks in the recent AI outbreaks in Delaware and Virginia, the current $CO_2$ methods are very labor intensive and includes biosecurity hazards.

Accordingly, there is a need for an alternative method to depopulate livestock that minimizes labor resources and contamination, while maximizing efficiency, health, biosecurity, and safety.

SUMMARY OF THE INVENTION

A method of depopulating livestock is provided. The method comprises restricting the livestock in a defined space, and depositing foam into the defined space, forming a foam blanket covering the livestock. The livestock can be avians, such as chickens, ducks, and turkeys. A device for making medium expansion foam comprising a high expansion foam generator having a fan, and a shroud shielding the fan from ambient air intake. The shroud limits the amount of ambient air incorporated into the foam during operation. The device can include an alternative gas input positioned to direct an alternative gas to the fan. The alternative gas is selected from the group consisting of carbon dioxide, nitrogen, argon, and mixtures thereof.

DETAILED DESCRIPTION OF THE INVENTION

Figure 1:
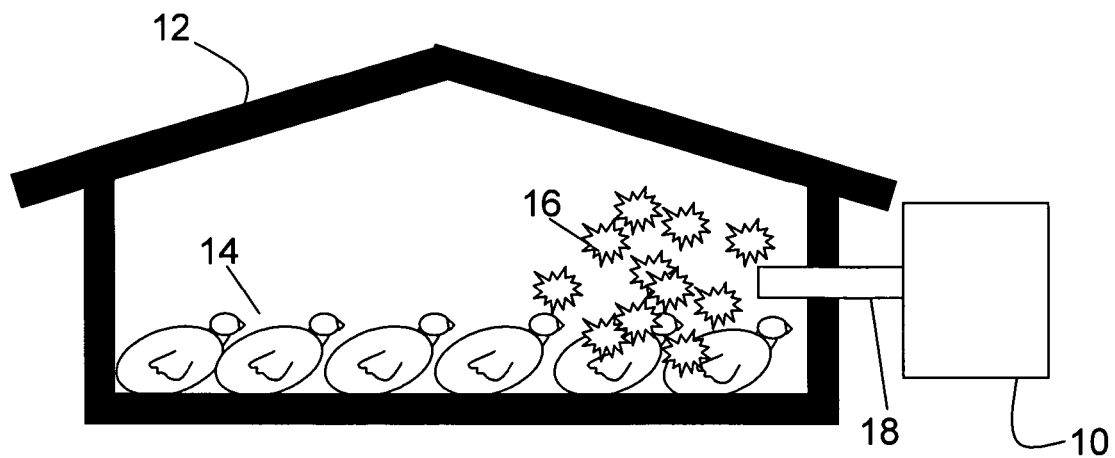
FIG. 1 is a schematic of a side view of a livestock house at the initiation of depositing foam inside the livestock house.

Alternative methods and devices for depopulating livestock are provided. The method includes using foam to physically occlude the airways of the livestock, first rendering the livestock unconscious, then causing death. The foam can be supplied in a variety of ways, and through various devices. Consistent with this process, the foam is deposited such that it creates a foam blanket that covers the targeted livestock population.

One embodiment includes restricting the livestock in a defined space. Typically, livestock will be housed in a pen or building. In the case of poultry, the birds are typically housed in a poultry house. Any containment, such as a pen or a house, serves to restrict the livestock in a defined space. The livestock may be further constrained to a smaller portion of the house to reduce the required coverage area. Once the livestock are contained in a defined space, foam is deposited into the space.

Depositing foam into the defined space can be done by a variety of means. Most commercially available foam generating systems are adapted for use in fire-fighting applications. One type of foam generators are known as high expansion foam generators. They use a fan to mix ambient air with foam concentrate and water. Expansion rate refers to the ratio of input water and foam to resulting foam output. Water-based foam is rated on expansion capability, and high expansion foam has an expansion of 200:1 or greater. Medium expansion foam has an expansion ratio between 20:1 and 200:1. Low expansion foam has an expansion ratio of 20:1 or less.

Water-based foam is created from water, air and foam concentrate. High expansion foam generators look similar to large fans, having blades that force air in the production of the foam. Water pressure, rather than a motor, is typically used to spin the fan and nozzles are distributed through the system to spray a mixture of foam concentrate and water into the air stream created by the fan. A fixed eductor or variable rate injection pump is used to proportion the flow of water to foam concentrate and the foam-water mixture does not expand until it reaches the air stream. The foam proportion on a high expansion foam generator is generally fixed, although the incoming water pressure and flow rate can be adjusted to alter the foam generation rate and volume. Medium and low expansion generators operate in a similar manner, but the air supply, water flow rate and water pressure are adjusted to provide the proper expansion ratio.

Foam concentrates consisting of standard surfactants are appropriate for use with the present invention. Several different foam concentrates, such as Ansul JET-X high expansion foam concentrate, Playtex (Westport, Conn.) MR BUBBLES bubble concentrate, and Procter and Gamble (Cincinnati, Ohio) DAWN soap are just a few examples of the foam concentrates tested. The range of expansion ratios can vary for foam concentrates, as some compositions provide high expansion ratios, and some low expansion ratios, so selection of the foam concentrate can influence the expansion ratio of the foam generated.

In addition to the foam generators based on using a fan to supply air, foam can also be formed using compressed air foam systems (CAFS). This technology is used extensively to generate foam for firefighting. Compressed air foam systems involve mixing water and foam concentrate together with a mechanical proportioning device. In a conventional foam system, aeration of the mixture occurs at a nozzle. With a compressed air foam system, aeration occurs by injecting compressed air into the mixture to cause expansion. The system requires a water pump as a prime mover, a foam proportioning system, and an air compressor. The water pump flow rate, foam proportioning rate, and air injection rate are normally adjustable on CAFS equipment.

In a typical CAFS configuration, the water pump, foam proportioning system and air compressor are located on a fire truck. The foam is formed at the truck, and forced through a hose to be deposited at the desired location. Compressed air foam systems increase the effectiveness of a given water supply for fire suppression, and can be used to provide a protective foam coating over structures to reduce the spread of fire. CAFS reduces both the water requirements and the weight of hoses, which in turn reduces the number of personnel required.

Compressed air foam systems are typically truck or skid mounted and can include a gasoline or diesel powered water pump, a foam eductor and a compressed air source. A standard fire hose can be used to distribute the foam through the defined space. Standard CAFS fire-fighting equipment does not need modifications for use in these depopulation methods.

Figure 2:
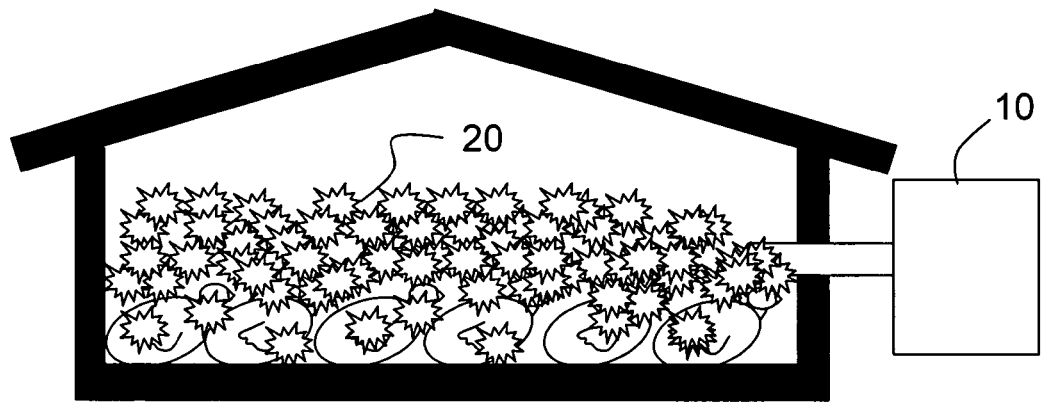
FIG. 2 is a schematic of a side view of a livestock house with a deposited foam blanket.

Referring to FIG. 1, the foam generator 10 can be positioned outside the defined space. In FIG. 1, the defined space is shown as a poultry house 12 containing poultry 14. The foam 16 is formed in the foam generator 10 and deposited through a foam guide 18 into the poultry house. Referring to FIG. 2, a foam blanket 20 is formed by depositing foam into the poultry house to a level sufficient to cover the poultry entirely. The thickness of the foam blanket is species and age specific. For chickens, the layer should be at least six inches above the birds.

Experimental results have shown that the foam blanket, with or without carbon dioxide gas, causes death of poultry by mechanically occluding the trachea, causing hypoxia. This is the same mode of action as other existing poultry depopulation methods. Experiments confirmed that the procedure does not drown the birds.

Figure 3:
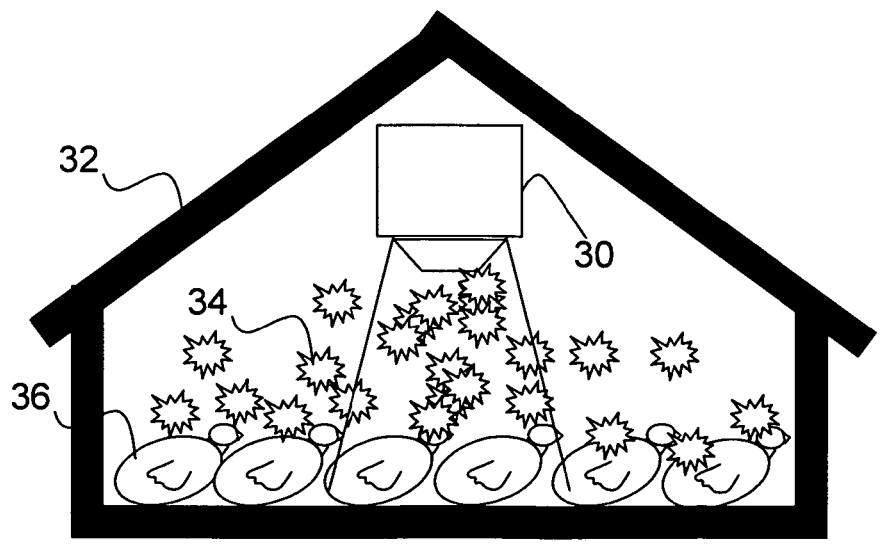
FIG. 3 is a schematic of a side view of a livestock house containing a stationary foam generator.

In one embodiment of the invention, the foam generator is located inside the defined space containing the livestock. Referring to FIG. 3, a foam generator 30 is positioned inside a poultry house 32 such that the foam 34 covers the poultry 36 as it is expelled from the foam generator. Fork lifts or similar equipment can be used to move stationary foam generators. Each foam generator can be self-contained and include the required water and foam to produce the desired amount of foam. Each generator would produce foam and cover a region around the generator. Multiple generators may be required in the defined space.

Figure 4:
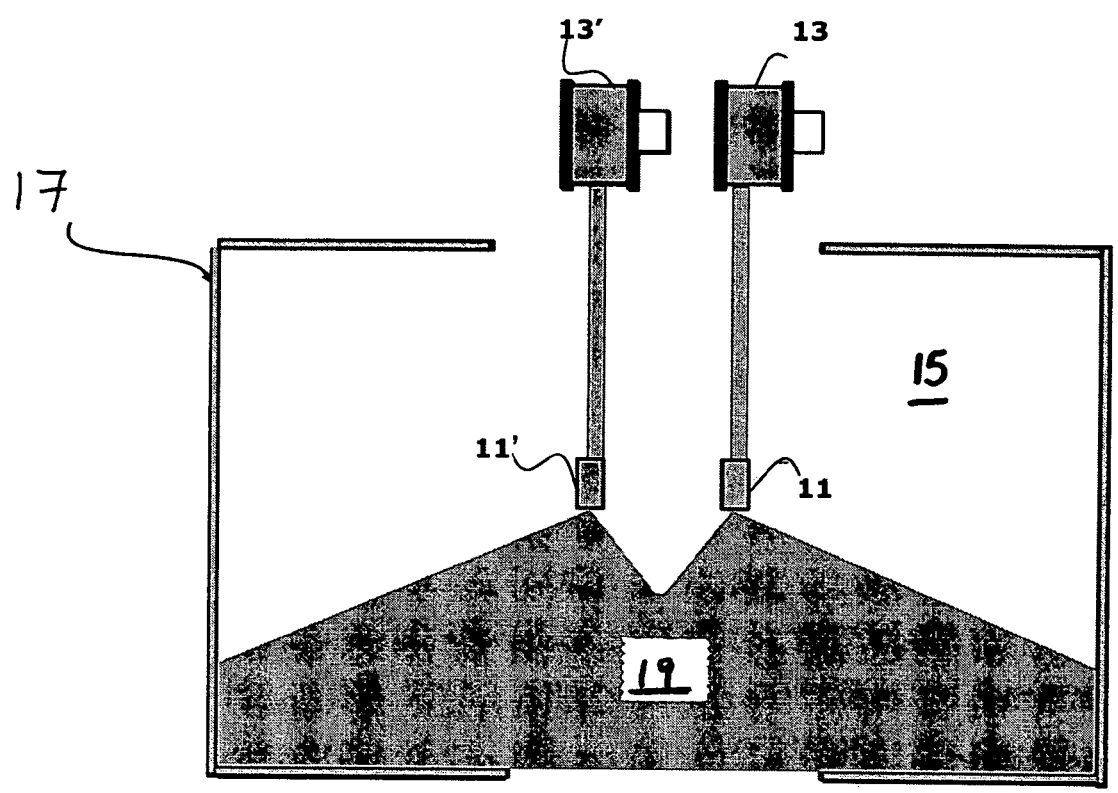
FIG. 4 is a schematic of an overhead view of a livestock house containing two foam generators.

In another embodiment, a foam generator may be positioned manually, on a cart or truck bed and the generator can travel through the confined space to distribute foam throughout a large area. With reference to FIG. 4, dual foam generators 11 and 11' can be positioned in a livestock house 17. The foam generators can be drawn across the house by retractable hose on reels 13' and 13. The shading 19 indicates the area of the livestock house that has been covered in a foam blanket, and the unshaded area 15 indicates the area that has yet to be covered in foam as the foam generators are drawn towards the hose reels 13 and 13'.

Medium expansion nozzle-based systems are also provided. With medium expansion nozzle-based systems, water and foam are premixed in a container or tank. The resulting foam concentrate and water mixture is pumped by a small gasoline or tractor mounted power take off (PTO) driven pump. The pressurized water and concentrate mix is pumped to the nozzle, which is used to generate a medium expansion foam. Premixed water and foam concentrate can damage pump seals and internal components. The resulting 36:1 medium expansion foam has been shown to be effective at depopulating chickens and turkeys. The nozzle-based system can be used to project the foam some distance away from the operator and through screens, windows or other open regions.

Figure 5:
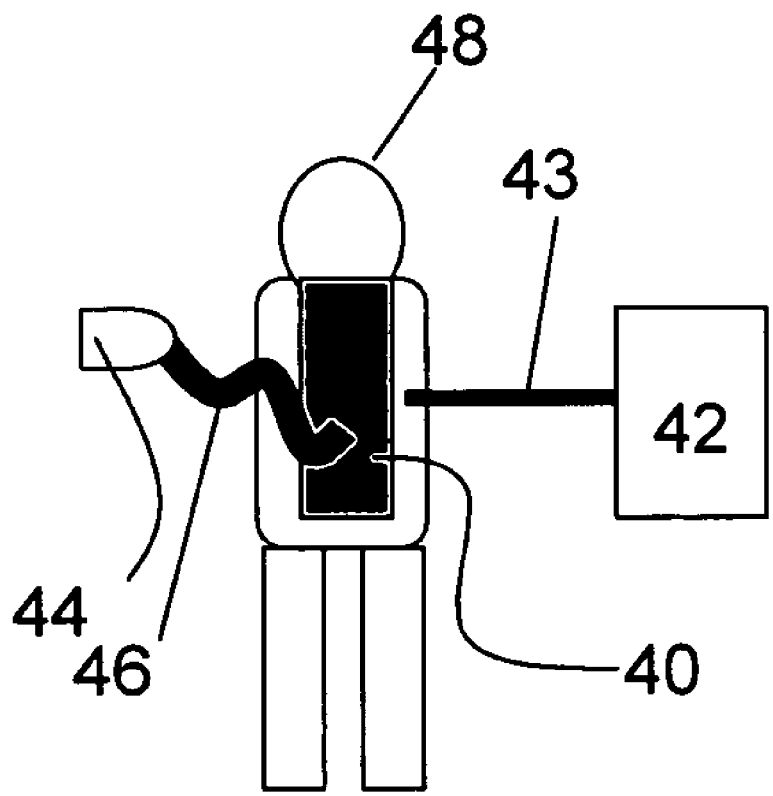
FIG. 5 is a schematic of a foam blower according to one embodiment.

Referring to FIG. 5, the foam may be deposited from a device that is portable and worn much like a backpack, similar to a gas-powered leaf blower. Such a device includes a foam generator 40 that is connected to a pump that pumps a mixture of water and foam concentrate 42 by a hose 43. A motor in the foam generator blows a mixture of foam concentrate and water to an aerator in a nozzle 44 at the end of a foam positioning hose 46. The operator 48 can be positioned outside the confined space or can be positioned inside the space. The portable unit provides the user mobility in applying foam to otherwise difficult to access areas.

Foam blowers are an option for some applications including backyard applications and isolated pockets of animals, such as birds. Foam blowers use a portable gasoline driven leaf-type blower connected to a water pump. The water and foam concentrate is provided via a water pump to the foam blower. A special discharge tube is added to the leaf blower to generate the required foam. The water pump is located outside the house, near the water and foam sources. Each operator inside the house is equipped with a backpack mounted foam blower.

Foam blowers are relatively portable and easy to set up. The maximum flow rates for foam blowers are relatively low in contrast to high or medium expansion foam generators. The lower flow rate makes foam blowers a less than satisfactory solution for large production houses. Foam blowers operate at the lower medium expansion range (50:1). For a typical 50'×500' poultry house, foam blowers are estimated to require 3 to 4 hours, 2 operators inside the house to operate the foam blowers, at least one operator outside the house to operate the pump, approximately 5,000 gallons of water and 100 gallons of foam.

Figure 6:
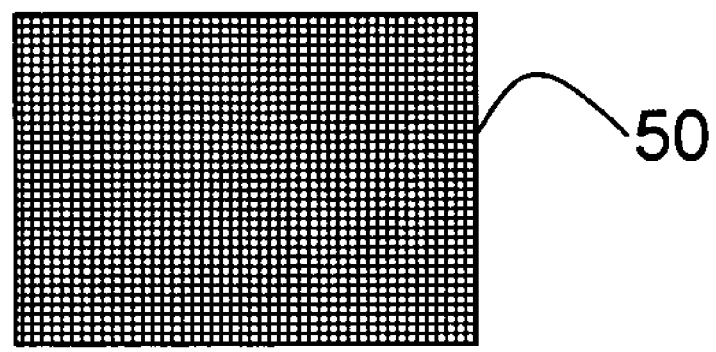
FIG. 6 is a schematic of a grating for forming foam bubbles.

Foam can be formed by pushing water and foam concentrate through a grating. The nozzle 44 or generator 10 contains a grating 50 as shown in FIG. 6. Gratings can be adjusted in mesh size, and used in combination with other gratings to provide the desired foam characteristics including bubble size and foam expansion ratio.

Figure 7:
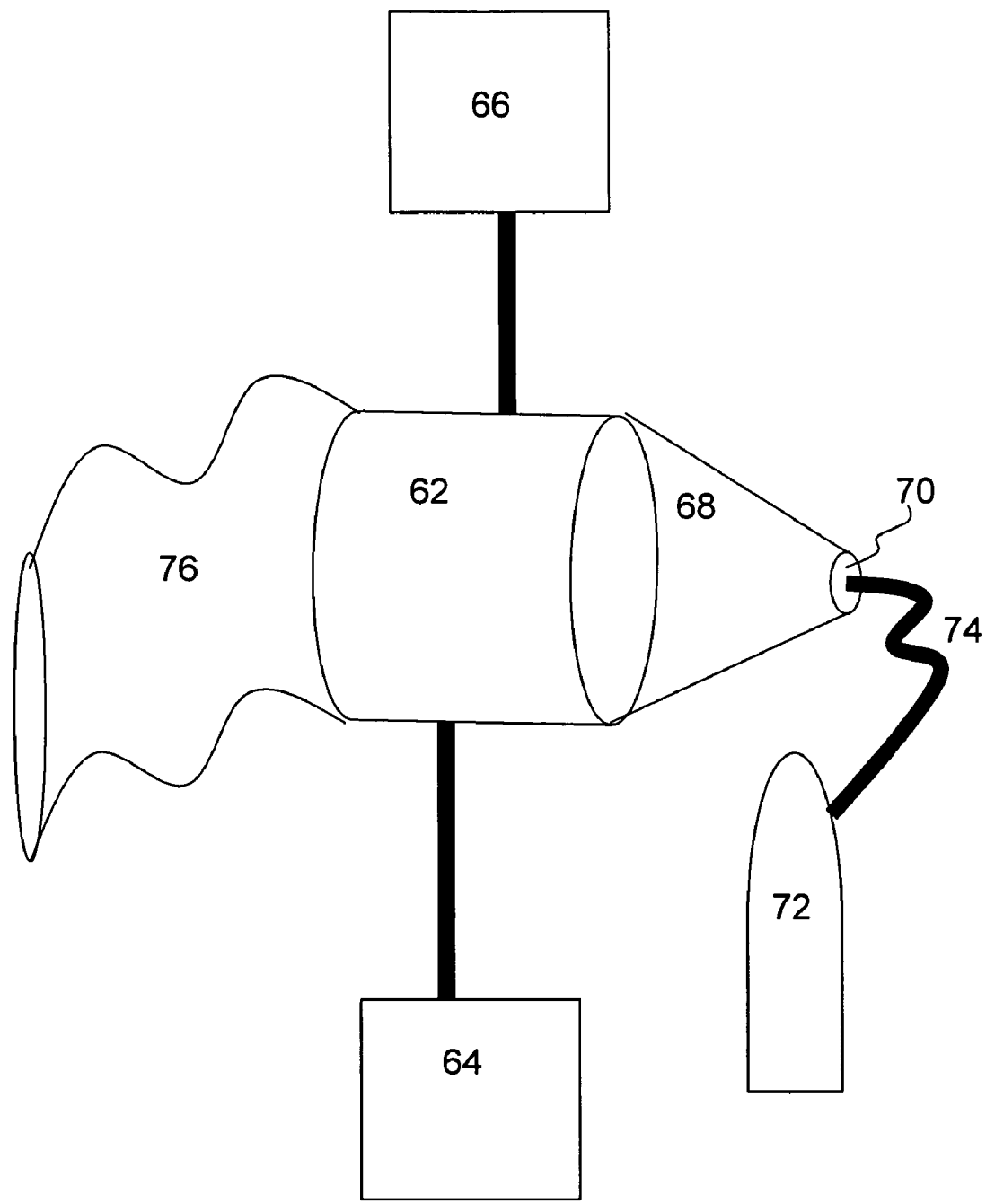
FIG. 7 is a schematic of a modified foam generator.

Referring now to FIG. 7, another embodiment of the invention includes a device for making a medium expansion foam. The device includes a high expansion foam generator 62 having a fan. Some appropriate foam generators include Ansul Mini-Fomax, Ansul PFG-M, Kidde, and Chemguard portable high expansion foam generators. These generators have a water source 64 and a source of foam concentrate 66 that feed into the fan. The generators have a large fan that is normally driven by water pressure. Nozzles are distributed around the fan to discharge water and foam concentrate into the air stream created by the fan. A fixed eductor or variable rate injection pump is used to proportion the flow of water to foam concentrate. A mesh screen located behind the fan is used to adjust the size of the bubbles. A foam guide 76 can be used to direct foam if necessary.

The foam generators are adapted with a shroud 68 that limits the air input to a small opening 70. The shroud shields the fan form ambient air intake, and the shroud limits the amount of ambient air incorporated into the foam during operation of the generator. Medium expansion foam can be formed using ambient air that accesses the generator through the restricted air opening 70. In another embodiment, medium expansion foam can be formed using an alternative gas. The alternative gas is provided through an input, such as a gas line, positioned to direct the alternative gas to the fan. In FIG. 7, an alternative gas source 72 is shown feeding gas into the foam generator 62 by a gas line 74. Appropriate alternative gases include carbon dioxide, argon, nitrogen, and mixtures of said gases among other appropriate gases.

The methods and devices described are appropriate for depopulating livestock, especially avians. The method is appropriate for depopulating poultry, including chickens, turkeys, and ducks. The method provides that a foam blanket covers the livestock, and that the foam induces a mechanical occlusion of the airways. Enriching the foam with an asphyxiating gas may improve performance in some situations, but is not required for successful depopulation.

These methods of depopulation are appropriate when livestock are suspected of carrying a zoonotic disease. In the case of avians, these methods are appropriate when the avians are suspected of carrying an avian disease. In the particular case of poultry, wetter, medium expansion foams can be preferable to high expansion foams. High expansion foam generators produce foam that is drier, and wet foam more reliably flows into the trachea of the birds. Additionally, as birds move, they create pockets in dry foam that don't exist with the use of wet foams.

The methods are useful in depopulating livestock without requiring the transport of infected birds outside of their defined space, such as a building. The methods are particularly helpful when the livestock building is structurally damaged, as the methods allow farm workers to safely depopulate the livestock without having to enter the structurally damaged building.

These methods can be used to simultaneously disinfect the buildings by adding a disinfectant, such as a peroxygen compound, to the foam. Additionally, foam compositions and settings can be optimized to facilitate on-site decomposition of the livestock carcasses. Water-based foam can be used to improve in house composting as a means of post-outbreak carcass disposal. In house composting is one of the preferred means of inactivating virus in infected carcasses. In house composting generally uses a mix and pile procedure and retains all material inside the house, improving biosecurity. Water is a critical component for in house composting of bird mortalities and additional water often has to be added to the compost pile to ensure satisfactory results. Experiments have shown that foam increases compost pile temperature, which is important to inactivate viral agents.

EXAMPLES

Example 1

Foam Depopulation Using a Modified High Expansion Foam Generator

Foam depopulation of chickens was done using a modified high expansion foam generator. An Ansul (Marinette, Wis.) Mini Fomax high expansion foam generator was modified to produce carbon dioxide ($CO_2$) enriched foam. In a typical fire suppression application, the foam generator uses a mix of water, foam concentrate and ambient air to create high expansion foam. Water was introduced into the system from a high-pressure source. The foam generator was hydraulically powered by water diverted to a nozzle that generates a high-pressure stream. The water stream caused a cast rotor to spin and the rotor that in turn rotates the fan to create an air flow from ambient air. The high-pressure water flow created a vacuum that extracts foam concentrate from an external tank. The water-foam concentrate mixture was atomized and introduced into the air stream where it expanded into foam that appears similar to a rich dishwashing liquid.

The foam generator was modified with a custom shroud to limit the entrance of ambient air into the fan. The shroud was designed with a conical shape and a hose/nozzle assembly from a carbon dioxide tank was attached at the apex. Although the shroud was not hermetically sealed, the design potentially increases the concentration of carbon dioxide in the foam mixture. With zero carbon dioxide gas in the foam mixture, the system operated as a high expansion foam generator.

A commercial carbon dioxide gas tank was used for testing with a 0-3445 kPa (0-500 psi) adjustable regulator to control the gas flow. To disperse the gas into the air-water-foam concentrate mixture, a high-pressure expansion nozzle was attached to the end of the hose at the foam generator end. The water and gas flows were manually controlled. Gas concentration was governed by application pressure (0 to 689 kPa, 0-100 psi), which determined application flow rate. Calibrations of gas application pressure to achieved carbon dioxide concentration in the foam were measured using Draeger Safety Inc (Pittsburgh, Pa.) carbon dioxide 1%/a-d diffusion tubes. Diffusion tubes used to record gas concentrations during carbon dioxide polyethylene tent trials saturated immediately, indicating 30+% achieved concentrations.

Example 2

Single and Dual Foam Generators

Two prototypes have been developed, a single foam generator and a dual foam generator unit. The prototype foam depopulation unit includes two pieces: a mobile foam generator cart and a powered hose reel. The hose reel is based on a KIFCO B210 hard hose traveler with 176.7 m of poly hose, a gasoline driven pump capable of 321 L/s at 689 kPa, a gasoline hose drive motor and a variable rate foam concentrate injection pump. The gasoline pump provided the required pressure and flow for the water. Immediately after the water pump, the foam concentrate was injected into the water stream via a variable rate injection pump to achieve the desired ratio of foam concentrate to water flow. This allows the main pump to pump water only, which reduces wear on the pump. A small gasoline engine powers the hose reel and can retract the rigid hose connecting the hose reel to the foam generator, allowing the generator to be pulled back through the poultry house. The foam/water mixture is sent to the cart mounted KIDDE (Exton, Pa.), CHEMGUARD (Mainsfield, Tex.), or similar high expansion foam generator tuned to produce medium expansion foam. An additional valve is provided at the foam generator to allow the onboard operator to control the flow of water to the foam generator. The entire system can be transported on a single trailer.

To use the system, the generator cart is dropped at one end of the poultry house and the hose reel is dropped at the other end of the poultry house. An electric winch, ATV or suitable vehicle is used to extend the rigid hose through the house. The hose is connected to the portable foam generator cart. Water can be supplied via water tankers, portable tanks, or by drafting from a surface water source. One operator wearing appropriate personal protective equipment rides onboard the foam generator cart to control the distribution of foam. A second operator operates the hose reel and monitors the foam and water supply. The second operator controls the speed of the hose reel, which gradually pulls the foam generator cart towards the hose reel. The two operators work in conjunction to build a layer of foam over the birds. After completing the house, the equipment can be power washed and disinfected prior to transport to the next facility.

For a typical 50'×500' poultry house, a large scale medium expansion generator system with a dual foam generator cart would require only 20 minutes to depopulate a single house, 1 operator inside the house to operate the foam generators, 1 operator outside the house to operate the hose reel, 4,000 gallons of water and 40 gallons of foam. With a single generator system, the time requirements would increase, however, the water and personnel requirements would remain the same. In addition, the single generator systems may not be as suitable for large scale houses as the dual generator systems.

Example 3

Depopulation Procedures for Poultry

A series of experiments were done to evaluate the depopulation methods on poultry, in particular chickens. Before testing began, the birds were moved into the euthanasia chamber or holding pen. After the birds were in place, foam was introduced into the chamber. The time to fill the chamber, the time for the birds to reach full immersion and the cessation time of the birds were recorded. The birds could not be viewed directly through the opaque foam. Observation of the foam and movement thereof determined cessation time. The consistency of the foam caused the surface of the foam to shift when there was any bird movement within the foam. When surface movement of the foam ceased, cessation was assumed.

Five minutes after the start of foam application, all birds were tested following AVMA (2001) guidelines for checking euthanized poultry. Cervical dislocation was used to extinguish any bird that was unconscious, but not clinically deceased at this time. If the birds were found to be unconscious at the five-minute test, then subsequent examinations were made at five-minute intervals until all of the birds were dead. All testing was performed under the approval and guidelines of the Agricultural Animal Care and Use Committee.

The polyethylene tent method, a method currently used by a portion of the poultry industry, was used as a control for the experiment. A polyethylene sheet was placed over the birds and the edges were weighed down to minimize escaping gases. Once the polyethylene sheet was in place, CO2 gas was pumped into the chamber under the sheet to depopulate the birds. Cessation times were measured directly, however, fill and immersion times were not recorded. One bird was selected at random at the five-minute mark and the clinical testing procedures described in under foam testing were followed.

A limited number of birds were used in a number of trials to test the effectiveness of the foam-based system for depopulation. For each trial, five healthy six-old week old broilers were placed into a 79 cm (w)×65 cm (h)×79 cm (l) (31 in×25.5 in×31 in) clear polycarbonate chambers and CO2 gas was introduced into the foam at graduated delivery pressures. For this phase the delivery pressures were 0, 177, 344 and 698 kPa (0, 25, 50 and 100 psi, respectively). The delivery pressures corresponded to achieved gas concentrations of 0%, 5%, 10% and 20%. Equipment limited the maximum achievable gas delivery pressure and, consequently, the maximum achievable concentration. All twenty broilers expired during this stage.

In all four trials, the birds ceased any observable activity in less than two minutes (Table 1). Testing demonstrated that with carbon dioxide delivery pressures less than 344 kPa (50 psi) the birds would be rendered unconscious, but did not guarantee death within five minutes. Surviving birds were eliminated by cervical dislocation. In all cases, the birds expired by the ten minute mark. Once the birds were unconscious, involuntary convulsions would begin. Once these convulsions ceased, the birds were considered to have expired.

TABLE 1

Summary of preliminary depopulation results, Example 3.

| Test | $CO_2$ Pressure (psi) | $CO_2$ Concentration (%) | Bird Activity Ceased (min:s) | 5-min Evaluation | 10-min Evaluation |
|---|---|---|---|---|---|
| 1 | 0 | 0 | 1:55 | Unconscious | Clinical death |
| 2 | 25 | 5 | 1:45 | Unconscious | Clinical death |
| 3 | 50 | 10 | 1:30 | Clinical death | n/a |
| 4 | 100 | 20 | 1:35 | Clinical death | n/a |

Example 4

Comparison of Depopulation Procedures for Poultry

Using similar methodology as in Example 3, three different depopulation methods were compared. The three methods tested were fire fighting foam with CO2, fire fighting foam without CO2, and the standard CO2-polyethylene tent method. All three methods were all shown to successfully kill the birds.

Six replications per treatment with three healthy six and one half week old broilers per replication were used. For each trial, three healthy 6½ week old broilers were placed into the chamber and foam (with or without CO2) or CO2 were introduced into the chamber. For the CO2 enriched foam, CO2 concentrations were 10% for six trials and 20% for one trial. To improve observation, a reduction chamber which forced the birds closer to the front wall of the chamber was used for the foam trials. The reduction barrier was not used during the CO2-polyethylene tent method. A total of 57 broilers were used in Experiment Two. In all 19 of the trials conducted, all but one of 57 broilers died in less than 4 min. Table 2 summarizes the results for each depopulation method.

TABLE 2

Summary of comparative depopulation methods

| Test | | Cessation (min:s) |
|---|---|---|
| Foam, 0% $CO_2$ | Average | 2:54 |
| | Std. Dev. | 0:28 |
| Foam, 10% $CO_2$ | Average | 2:40 |
| | Std. Dev. | 0:18 |
| Foam, 20% $CO_2$ | | 2:09 |
| $CO_2$-polyethylene tent method | Average | 2:08 |
| | Std. Dev. | 0:32 |

TABLE 3

Summary of field conditions depopulation results

| Test | | Fill Time (min:s) | Head Coverage (min:s) | Cessation (min:s) | Unconscious (min:s) |
|---|---|---|---|---|---|
| Foam, | Average | 0:47 | 0:59 | 4:17 | 3:29 |
| 0% $CO_2$ | Std. Dev. | 0:49 | 0:50 | 1:44 | 2:02 |
| Foam, | Average | 2:01 | 2:20 | 4:38 | 2:37 |
| 10% $CO_2$ | Std. Dev | 0:17 | 0:23 | 0:27 | 0:17 |
| $CO_2$- | Average | n/a | n/a | 3:47 | 3:47 |
| polyethylene | Std. Dev. | n/a | n/a | 0:12 | 0:12 |

General observation of the experiments indicated that the fire fighting foam process was comparable to the currently CO2-polyethylene tent method. Average cessation times were under 3 minutes for all testing methods. The average time for the CO2-polyethylene tent method was the shortest, but individual cessation times were highly inconsistent ranging from 1:22 to 2:55 (minutes: seconds). Of the foam methodologies, the trials in which CO2 was introduced had the most consistent cessation times. The differences between treatments were analyzed using Microsoft Excel ANOVA procedure and the differences were not statistically significant at the 5% level.

Observable indicators of distress were apparent during the CO2-polyethylene tent method. When the broilers were subjected to the CO2 gas under the polyethylene sheet, vocalization, and visible agitation could be seen as the birds lost consciousness. In the case of the foam tests, the birds appeared to remain calm as the foam was introduced into the chambers. Even as the foam began to engulf the birds, in most cases the birds showed no signs of distress. Any birds that were in the path of foam entering the chamber typically reacted to the foam pouring onto their heads, but calmed after moving out of the path of the foam. In the foam depopulation trials, the convulsions agitated the foam, in some cases causing the foam level to decrease over the birds.

Example 5

Field Conditions for Depopulation Procedures for Poultry

In this example, simulated actual field conditions in poultry houses were used. The tests were conducted on birds in poultry pens inside of a broiler house. Three treatments (foam with CO2, foam without CO2, and CO2-polyethylene tent) were used, with three replications of 20 broilers, 6 weeks of age, per treatment. For the foam tests, the wooden holding pens were lined with plastic sheeting to retain the foam and the birds were subsequently moved into the pen. An ad hoc reduction chamber was used to restrict the movement of birds before the introduction of the foam and during testing. A total of 180 broilers were used The broiler house environment more accurately simulates the conditions under which emergency depopulation would occur. The results of this test are shown in table 3. The differences between treatments were analyzed using Microsoft Excel ANOVA procedure and the differences were not statistically significant at the 5% level.

Comparing the average cessation times, it is apparent that the CO2-polyethylene tent method took longer than foam with or without CO2. There are numerous reasons for this observed change in CO2-polyethylene cessation times. The polyethylene sheets had to cover a much larger area than in the chambers and this requires more time for the CO2 gas to disperse under the sheet. Also, with the larger area, more CO2 may have escaped from under the sheets.

Example 6

Cause of Death Using Foam Depopulation Procedures for Poultry

A laboratory evaluation of the cause of action of the foam method was conducted. The three treatments (CO2-polyethylene tent method, foam without CO2, and foam with CO2) were compared, with 10 replications of one bird per replication for each method. Each treatment drew from a pool of mixed age birds (5 and 10 weeks old) and the bird ages were evenly distributed through the treatments, with seven to eight 5-week old and two to three 10- to 11-week old broilers totaling 10 per test method.

Each bird was instrumented with ECG sensors. BIOPAC Systems, Inc. (Goleta, Calif.) BioPac Student Laboratory edition ECG monitoring pads were secured onto the left leg, right wing and right leg. The ECG equipment was used to determine heart cessation of activity (time of death) of the bird.

Foam was created using 160 ml Ansul (Marinette, Wis.) Jet-X high expansion foam concentrate, 6 L tap water and one Fort Dodge Animal Health (Fort Dodge, Iowa) Hi-Light blue dye tablet. Dye was added to assist in the postmortem gross and microscopic observations of the trachea, syrinx, and lungs. The foam was aerated and mixed using compressed air (foam without CO2) or compressed carbon dioxide gas (foam with CO2). The dyed foam mixture was re-agitated prior to use. For the foam trials, the birds were prepared individually and placed inside a 113 L chamber pre-filled with foam. For foam, cessation time was recorded as the difference between the time from head coverage to cessation of activity, as measured by the ECG.

The CO2 polyethylene tent treatment was used as a control for the experiment. For the polyethylene tent method, the broilers were placed inside a 79 cm (w)×65 cm (h)×79 cm (l) clear polycarbonate chamber equipped with a CO2 discharge system and covered with an opaque tarp. No dye was added to the CO2 gas used for the polyethylene tent method. A polyethylene sheet was placed over the birds and the edges were weighed down to minimize escaping gases. Carbon dioxide was applied for approximately 60 seconds, and the CO2 concentration (61%) was calculated from the flow rate measurements. Cessation time was the difference between start of gas application to cessation of activity, as measured by the ECG.

At five minutes post treatment, all birds were tested to confirm there was no heart beat. Cervical dislocation was used to euthanize any bird that was unconscious, but not clinically dead. All testing was performed under the approval and guidelines of the Agricultural Animal Care and Use Committee.

Post treatment, the broiler was removed from the CO2 chamber or foam chamber and postmortem blood samples were removed using cardiac puncture. Blood samples were drawn within two minutes after treatment. Pretest and postmortem blood samples were chilled on ice, centrifuged to recover plasma and stored at −28° C. and analyzed for corticosterone steroid levels. Necropsies were performed immediately after treatment. Tissue samples of the trachea and lung were removed from each bird for histology.

The cessation of activity times were extracted from the resulting ECG data files for each study. Foam with CO2 required 73 s for cessation, foam without CO2 required 64 s and CO2 polyethylene tent required 139 s. Foam with and without CO2 were 47% and 54% faster, respectively, than the CO2 polyethylene tent treatment. The differences in cessation time were analyzed using Microsoft (Redmond, Wash.) Excel ANOVA and the differences between the foam and polyethylene tent treatments were statistically significant at the 5% level. The differences between the foam treatments were not significant, indicating that the presence of CO2 in the foam did not change the cessation time.

Post mortem examination through necropsy and histology observed blood in the lumen of the trachea, syrinx, and primary bronchi of a few birds, as shown in table 4. The finding of blood is common in chickens undergoing CO2 depopulation and results from mucosal capillary leakage. One bird had consolidation in the left lung and histology results revealed bronchopneumonia as the cause. The bronchopneumonia was not related to the testing performed in the course of the experiment. In the ten birds in the CO2 polyethylene tent treatment, no blue dye was present in the tissue, as no dye was used in this treatment group.

In the 10 birds in the foam without CO2 treatment, blue dye was consistently present in the trachea. The reason that the dye was not present in the lung relates to the foam dye mixture being blocked by the narrow lumen of the syrinx, and/or just blocked by accumulating in the lumen of the trachea.

In the 10 birds in the foam with CO2 treatment, dye was present in the trachea of 9 out of the 10 broilers. Dye was present in the lung of at least 3 out of the 10 birds. The reason the dye entered some of the lungs in this group, but not the group without CO2 is unclear. It may be that CO2 and dye were inspired before the foam could accumulate to a significant degree in the trachea or syrinx. The histopathology results made show that the fixation process removed the dye and foam from the respiratory system.

Blood, represented by red blood cells (RBCs) and mostly lacking the fluid portion, was present to some degree in the trachea, syrinx, and bronchial tree in all three groups. The presence of blood in the respiratory lobules probably relates to anoxic changes in the endothelial cells of the thin air-blood barrier permitting leakage of blood into the air capillaries with progression to the lumen of the parabronchi (tertiary bronchi) and larger branches of the respiratory tree. Other current depopulation methods including cervical dislocation and CO2 administration both result in blood accumulation in the respiratory tree to include the parabronchi. The birds treated with the foam and CO2 treatments died of hypoxia and there was no evidence of drowning in any of the birds sampled.

TABLE 4

Summary of histology results

| Treatment | Dye[a] | | Blood | | | |
|---|---|---|---|---|---|---|
| | Trachea | Lungs | Trachea | Syrinx | Bronchi | Lungs |
| Foam without $CO_2$ | 10 | 0 | 0 | 0 | 5 | 10 |
| Foam with $CO_2$ | 9 | 3 | 0 | 2 | 2 | 10 |
| $CO_2$-Polyethylene | N/A | N/A | 3 | 2 | 6 | 10 |

[a]Results are out of 10 birds per replication.

Example 7

Simulated Field Test of Foam Depopulation System for Poultry

Two test treatments (water based foam and polyethylene tent method) were directly compared under field like conditions. A 11.58 m×14.63 m (38 ft.×48 ft.) poultry house was divided into six pens, with 208 five week old broilers (n=1200) per pen.

For each test method, one bird per trial was instrumented with a BIOPAC Systems, Inc. BioPac Student Laboratory edition ECG monitoring equipment and PCB Piezotronics, Inc 352C66 accelerometer as in Example Six. Blood samples were drawn from ten uniquely identified birds per pen pre-test and post-test.

Portable CO2 and confined space (O2, CO, explosive gas) meters were used to monitor ambient air quality during testing. No discernable changes in O2 level were detected during the initial polyethylene tent method and as a result, confined space measurements were only recorded during one trial. Carbon dioxide measurements were recorded during all six trials, providing background, peak and removal readings for polyethylene and background, peak and agitation for foam test.

For the polyethylene tent method, a gas injection nozzle was attached to a heavy metal object and located in the approximate center of the pen. Opaque 6-mil polyethylene sheet material was placed over the birds and secured on all sides. After coverage of the birds, CO2 gas was allowed to fill the tent chamber. The gas was stopped and the tarp removed two minutes after all bird movement had ceased.

For the foam trial, commercially available compressed air foam system (CAFS) fire fighting apparatus was used to generate the compressed air foam. At the discharge of the pump, a gas injection nozzle was installed in the hose fitting, allowing CO2 to be injected into the created foam. No modifications were made to the actual pumping equipment. A standard fire fighting hose and nozzle was used to apply the foam to the birds. National Foam Knockdown class A foam was used. During foam application, the foam was sprayed against the wall or ceiling of the house and allowed to flow around and onto the birds. The direct stream of the pressurized foam was not applied directly to the birds. Black polyethylene sheet was used to separate the pens to prevent the foam from flowing from pen to pen. Portable poultry pens were used to confine the birds to a smaller portion of the pen (2.13 m×3.45 m, 7 ft.×11 ft 4 in.). Pre-test and post-test surface litter samples were drawn from the appropriate pens. Post-test samples of the foam were drawn from each trial for CO2 concentration.

The experimental method was effective and able to successfully euthanized the birds. The method required less active personnel and exposure to conditions.

Both the experimental and control methods were able to successfully euthanized the birds. The foam method was faster (average 4:34 m:ss) than the conventional polyethylene tent method (8:58 m:ss) as shown in Table 5. The times shown represent the time at which the process was started, all movement ceased and the polyethylene tarp was removed. The difference in cessation times between methods was statistically significant at the 5% level.

TABLE 5

Comparison of cessation time between foam methods and the polyethylene tent method

| Trail | Method | No. of Birds Start | No. of Birds Survival | Time Start (m:sec) | Time End (m:sec) |
|---|---|---|---|---|---|
| 1 | Polyethylene tent | 208 | 0 | 1:02 | 9:51 |
| 2 | Polyethylene tent | 208 | 0 | 0:37 | 8:41 |
| 3 | Polyethylene tent | 206 | 1 | 1:03 | 8:23 |
| Avg | Polyethylene tent | | | 0:51 | 8:58 |
| Std. Dev. | Polyethylene tent | | | 0:21 | 0:46 |
| 4 | Foam with $CO_2$ | 208 | 0 | 1:44 | 6:21 |
| 5 | Foam with $CO_2$ | 208 | 3 | 0:08 | 3:20 |
| 6 | Foam with $CO_2$ | 206 | 0 | 2:02 | 4:01 |
| Avg | Foam with $CO_2$ | | | 1:18 | 4:34 |
| Std. Dev. | Foam with $CO_2$ | | | 1:01 | 1:35 |

In trial 3 (polyethylene tent), one bird located within CO2 filled polyethylene tent survived past the removal of the protective sheeting. In trial 5, three birds that were inside the pen were able to stand high enough for their heads to clear the foam. The birds were moved to remain within the foam. Once moved, the birds did not survive the trial.

Fire fighting foam is delivered at relatively high pressure (approximately 689 kPA, 100 psi). The delivery pressure caused concern over potential damage and/or increased stress due to the force of the impact. As a result, the foam was applied against a side wall (trial 4 and 5) and to back wall (trial 6) and allowed to flow over the birds. This is a conventional fire fighting technique for flammable liquids and this allowed coverage of the birds without direct application onto the birds.

In trial 4, an error in testing lead to no CO2 entering the system. In trials 5 and 6, the achieved CO2 level was 1%. The CO2 content in the ambient air was monitored for human health concerns and is shown in Table 6. Because of the ambient conditions (95+F, 90% humidity), all equipment doors were open and the house was well ventilated. With the polyethylene tent method, CO2 concentrations were higher (3712 ppm) when the polyethylene was removed than when polyethylene tent was being filled (1592 ppm). Although the average numbers for the three trials were below human health concern levels, during testing, a peak of 5584 ppm was achieved during one trial. With the foam method, peak CO2 concentrations (1320 ppm) were achieved as the birds went through convulsions, breaking the bubbles in the foam.

TABLE 6

Comparison of gas levels between foam methods and the polyethylene tent method

| Trial | Method | $CO_2$ level Peak | re-moval | re-moval | Delivered Water L (gal) | Foam L (gal) | Air $M^3$ $(ft)^3$ |
|---|---|---|---|---|---|---|---|
| 1 | Polyethylene Tent | 608 | 1679 | 3491 | N/A | N/A | N/A |
| 2 | Polyethylene Tent | 634 | 1768 | 5584 | N/A | N/A | N/A |
| 3 | Polyethylene Tent | 525 | 1330 | 2060 | N/A | N/A | N/A |
| Avg. | Polyethylene Tent | 589 | 1592 | 3712 | N/A | N/A | N/A |
| Std. Dev. | Polyethylene Tent | 57 | 232 | 1772 | N/A | N/A | N/A |
| 4 | Foam with CO2 | 662 | 873 | 661 | 1175.6 (311) | 11.7 (3.1) | 17.61 (622) |
| 5 | Foam with CO2 | 819 | 1201 | 1755 | 272.1 (72) | 3.4 (0.9) | 4.07 (144) |
| 6 | Foam with CO2 | 677 | 1238 | 1545 | 268.4 (71) | 3.4 (0.9) | 4.02 (142) |
| Avg. | Foam with CO2 | 719 | 1104 | 1320 | 270.3 (71.5) | 3.4 (0.9) | 4.05 (143) |
| Std. Dev. | Foam with CO2 | 87 | 201 | 581 | | | |

The water, foam and air numbers were recorded using a totalizer. The results for Trial 4 include adjustments made before the test. Trial 4 numbers are not included in the statistics.

Surface litter samples were analyzed from the foam tests. The moisture content was higher than previous tests due to a difference in the sample collection methodologies. There were significant differences between the pretest (29.0%) and post test (64.4%) moisture levels. The litter moisture samples were collected from the top surface of the litter rather than from the complete litter profile. The samples were higher than previous samples collected during foam testing.

Example 8

Validation of Prototype Filed Depopulation System

Foam was generated using the single foam generator system described in Example 2. National Foam (Exton, Pa.) Hi-Ex foam concentrate was used.

Prior to bird testing, a 2-part experimental procedure was used to determine the appropriate experimental protocol based on the initial testing parameters. The foam delivery rate (and effective concentration) and water delivery pressure were systematically varied to determine the optimal foam. In addition, the multiple discharge screens were tested on the foam generator to enhance bubble nucleation. Based on these tests, two viable foam compositions and a control method were selected for validation testing with birds.

A randomized block procedure was used to test Treatment×Age interaction. Commercial broilers of three ages (2 weeks, 4 weeks and 8 weeks) were used. Three treatments were used for euthanasia. Foam A was created using a 1% foam concentration, 689 kPA (100 psi) discharge water pressure, 321 L/m (85 GPM) discharge flow rate, a standard Ansul foam generator shroud and no obstruction to the airflow entering the generator. Foam A was created using a 1% foam concentration, 689 kPA (100 psi) discharge water pressure, 321 L/m (85 GPM) discharge flow rate, a standard Ansul foam generator shroud and 69% reduction in airflow entering the generator. The CO2-Polyethylene tent procedure was used as a control. Between changes in foam concentration, the system was purged with water.

In each replication, two birds of the appropriate age were fitted with an accelerometer and placed within a chamber. Foam was applied to the chamber and birds. Cessation of activity of the birds was monitored through the use of an accelerometer mounted on the bird. Each of the two birds in the trial were fitted with a single PCB Piezioelectric (Depew, N.Y.) accelerometer that was securely attached to the right leg of the bird. The accelerometer outputs were recorded independently using National Instruments (Austin, Tex.) PCI-6036E data acquisition card and custom written National Instruments LabVIEW (Austin, Tex.) data acquisition and analysis software The use of accelerometers to determine cessation of activity had been tested in previous experiments and provides a means of measuring the cessation of activity within the foam. Cessation of activity was defined as the difference between time that the birds were exposed to the treatment and the last movement of the bird. Bird activity was timed for 300 s. If the bird was alive at the end of the 300 s data collection period, the bird was placed into a 113 L container of foam and bird activity evaluated at 10 minutes post treatment. All testing was performed under the approval and guidelines of the Agricultural Animal Care and Use Committee.

In this experiment, the commercial scale foam equipment was shown to be successful at depopulating birds of any age.

Example 9

Comparison of Two Sample Foam Depopulation Systems

Two sample foam depopulation systems were evaluated for their ability to depopulate meat type chickens. The first system was a dual foam generator of the type used in Examples 2 and 8. Chemguard high expansion foam was used. The second system used was a medium expansion nozzle system. The medium expansion nozzle system uses a gasoline powered pump capable of 200 gpm at 130 psi to draw water from a portable water tank premixed with foam concentrate. The pump was connected to two Spumifer 95-120M nozzles via standard firehose (1½" NHT). One operator was required to operate the gasoline powered pump while one operator was required to operate each foam nozzle. The nozzles were used to project the foam inside the house through the sidewall curtains and doors. Phos-Check forestry foam was used.

Each system was used to depopulate an equivalent number of birds (2,500 seven week old broilers) and area (41'×63'). The time required for head coverage and cessation of activity was recorded manually. Water and foam consumption were estimated from pump flowrate versus overall run time.

The dual foam generator system was able to successfully depopulate the birds. The foam generator required 915 gallons of water and 9 gallons of foam to depopulate the birds and fill the required region. The system required 5:03 (m:s) to cover the heads of all birds. Cessation of activity was recorded manually and occurred at approximately 11:06 (m:s). Survivability was recorded as the number of birds still alive after the foam began to degraded. For the dual foam generator system, survivability was 3/2500. The calculated expansion ratio was 140:1.

The medium expansion nozzle system was also able to depopulate the birds. The medium expansion nozzle system used similar, but slightly higher amounts of water (973 gallons) and foam (10 gallons). The system did allow distribution of the foam through the windows and doors. The medium expansion nozzle system required 4:52 (m:s) to cover the heads of all birds and cessation of activity was observed at 8:56 (m:s). For the medium expansion nozzle system, survivability was 1/2500. The calculated expansion ratio was 36:1.

These results suggest that depopulation of a whole house of 2500 birds would require 4,000 gallons of water using the foam generator system. The medium expansion system would require close to 8,000 gallons of water to fill the same space. Regarding timing, these results suggest that the foam generator would require 47 minutes to depopulate a whole house, while a single medium expansion nozzle would require 180 minutes.

Example 10

Evaluating the Impact of Foam on Composting

Example 10 was conducted following the protocol set forth in Example 8. Three treatments were used (Foam 1—Chemguard, Foam 2—Phos-Check, and No Foam). The birds from Example 8 were used to create a continuous compost pile, yet the birds from the foam treatments were kept separate in the compost pile from birds that were collected from a poultry processing plant that were dead on arrival (the no-foam treatment control birds).

Ten, five-week-old broilers per treatment were inoculated with the LaSota strain Newcastle disease virus, euthanized, tagged and included in each compost pile. These inoculated birds were removed from the sample pile on days 0, 1, 2, 3, 6 and 14. Tissue samples from the birds were removed and tested for virus activity. One sample tested positive for virus activity. That was a sample recovered Day 1 in the no foam treatment control. All other samples tested throughout the experiment tested negative for virus activity.

The use of fire fighting foam does not adversely affect compostability. Foam compost temperatures were higher than the no-foam control pile. Near the surface of the windrow (one-inch depth), the foam pile was 121° F. and the no-foam pile was 113° F. Similarly, at the one-foot depth the foam pile was 139° F. and the no-foam pile was 128° F. During the first 14 days (prior to turning) at the three-foot depth, the foam pile was 119° F. and the no-foam pile was 107° F. The higher temperatures help to promote virus inactivation.

Example 11

Corticosterone Levels of Birds Before and After Depopulation

Corticosterone is commonly relied on as an avian stress hormone. To evaluate bird stress during depopulation, pre-test and post-mortem samples were collected. The foam method with and without CO2 was compared to the polyethylene tent method. Each bird was instrumented with ECG sensors. BIOPAC Systems, Inc. (Goleta, Calif.) BioPac Student Laboratory edition ECG monitoring pads were secured onto the left leg, right wing and right leg. The ECG equipment was used to determine heart cessation of activity (time of death) of the bird. Blood samples were drawn from ten birds per treatment pre-test and post-mortem. Corticosterone assays were conducted using 25 µl serum diluted in 75 µl of steroid diluent; samples were run in duplicate following the methodologies outlined in the ImmuChem (MP Biomedicals, Irvine, Calif.) Double Antibody I125 Corticosterone DA Kit. Precipitates were counted in a gamma counter for 1 min. The assay, validated for precision (CV=0.2%) and parallelism ($P>0.05$), was sensitive to 0.125 ng/ml. Intra-assay variability was 2.0%, and inter-assay variability was 0.5%. Corticosterone steroid levels were analyzed using SAS (SAS Institute, Cary, N.C.) Proc Mixed with Tukey-Kramer analysis.

Corticosterone levels were higher pretreatment than postmortem. There was a statistically difference in corticosterone level between treatments prior to the treatments. There was no statistically significant difference between postmortem corticosterone levels for the different treatments. The pretreatment differences can be explained by the conditions of the experiment. The polyethylene tent control method was performed prior to the foam testing. The day of the foam testing, there were additional guests in the poultry house, increased ambient noise (diesel fire pump prime mover) and human movement into the pens. During foam testing, observers were located inside the adjacent pens to record video and still images. In addition, immediately after euthanasia, there was movement through the pens to rapidly recover specifically marked birds for postmortem blood draws. The experimental conditions explain the increase in pretreatment corticosterone levels.

Figure 8:
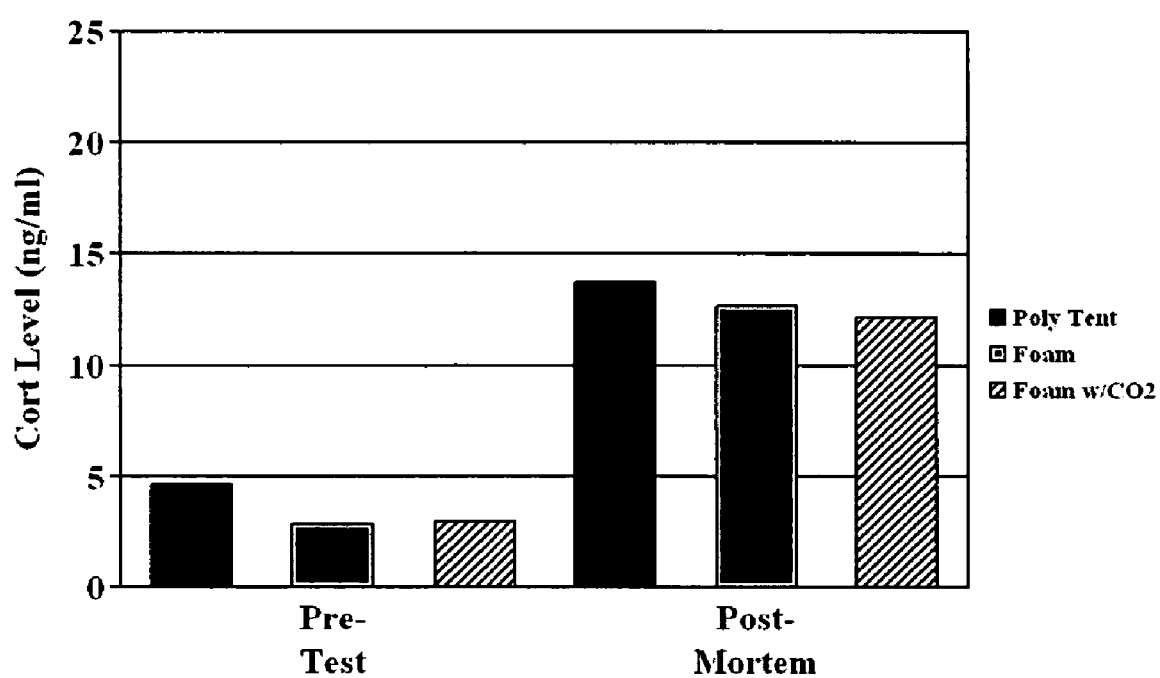
FIG. 8 is graph of corticosterone levels in chickens.

There was no statistically significant difference in pretreatment and postmortem corticosterone steroid levels, as shown in FIG. 8. Corticosterone levels were higher ($P<0.05$) post mortem than pretreatment. The differences between all three treatments were not statistically significant. There is no apparent difference in stress as measured by corticosterone level between the treatments. The corticosterone levels were similar to studies in which birds were subjected to catching stress.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of depopulating livestock comprising:
   a. restricting the livestock in a defined space; and
   b. depositing foam into the defined space, forming a foam blanket covering the livestock.
2. The method of claim 1 wherein the livestock are avians.
3. The method of claim 2 wherein the avians are poultry.
4. The method of claim 2 wherein the avians are selected from the group consisting of chickens, turkeys, and ducks.
5. The method of claim 4 wherein the avians are chickens.
6. The method of claim 4 wherein the avians are ducks.
7. The method of claim 1 wherein the foam blanket extends at least six inches over the livestock.
8. The method of claim 1 wherein the foam blanket induces mechanical occlusion of the livestock airways.
9. The method of claim 1 wherein the foam is enriched with an asphyxiating gas.
10. The method of claim 9 wherein the asphyxiating gas is selected from the group consisting of carbon dioxide, nitrogen, argon and mixtures thereof.
11. The method of claim 10 wherein the gas is carbon dioxide.
12. The method of claim 1 wherein the livestock are known or suspected of carrying a zoonotic disease.
13. The method of claim 12 wherein the livestock are avians, and the avians are suspected of carrying an avian disease.
14. The method of claim 1 wherein the defined space is a building.
15. The method of claim 14 wherein the defined space is a structurally damaged building.
16. The method of claim 1 wherein the defined space is a portable enclosure or pen.
17. The method of claim 1 further comprising depositing disinfectant with the foam.
18. The method of claim 17 wherein the disinfectant is a peroxygen compound.
19. The method of claim 1 wherein the depositing of the foam comprises moving a foam generating device through the defined space.
20. The method of claim 19 wherein the deposition of the foam is achieved by generating foam outside the space and then depositing the foam into the defined space through openings including doors, windows or structural damage.
21. The method of claim 1 wherein the method comprises forming the foam using a compressed air foam system.
22. The method of claim 1 wherein the method comprises forming the foam by pushing water and foam concentrate through a grating.
23. The method of claim 22 wherein the grating resides in a nozzle, and the foam expels from the nozzle.

* * * * *